United States Patent
Wallace

(12) 
(10) Patent No.: US 7,677,734 B2
(45) Date of Patent: Mar. 16, 2010

(54) AUDIOVISUAL DISTRACTION IN PATIENTS UNDERGOING SURGERY WITH REGIONAL ANESTHESIA

(76) Inventor: Arthur Wallace, 227 Lucas Park Dr., San Rafael, CA (US) 94903

( * ) Notice: Subject to any disclaimer, the term of this patent is extended or adjusted under 35 U.S.C. 154(b) by 1377 days.

(21) Appl. No.: 11/101,728

(22) Filed: Apr. 8, 2005

(65) Prior Publication Data

US 2005/0235422 A1 Oct. 27, 2005

Related U.S. Application Data

(60) Provisional application No. 60/560,882, filed on Apr. 9, 2004.

(51) Int. Cl.
 *G03B 31/00* (2006.01)
 *G02B 27/14* (2006.01)
 *G09G 5/00* (2006.01)

(52) U.S. Cl. ............................. 353/18; 359/630; 345/8; 348/115

(58) Field of Classification Search .................. 353/18, 353/122; 359/292, 630; 345/8, 32; 351/201; 348/61, 115; 600/27
See application file for complete search history.

(56) References Cited

U.S. PATENT DOCUMENTS

| | | | |
|---|---|---|---|
| 4,282,864 A | 8/1981 | Pizer | |
| 5,412,419 A | 5/1995 | Ziarati | |
| 5,517,278 A | 5/1996 | Takahara et al. | |
| 5,589,846 A * | 12/1996 | Kobayashi | 345/8 |
| 5,706,070 A | 1/1998 | Reich et al. | |
| 6,275,340 B1 | 8/2001 | Brown | |
| 6,469,683 B1 | 10/2002 | Suyama et al. | |
| 6,496,161 B1 * | 12/2002 | Tanaka | 345/8 |
| 6,538,624 B1 | 3/2003 | Karasawa et al. | |
| 6,563,626 B1 | 5/2003 | Iwasaki | |
| 6,640,127 B1 * | 10/2003 | Kosaka et al. | 600/426 |

* cited by examiner

*Primary Examiner*—Georgia Y Epps
*Assistant Examiner*—Magda Cruz
(74) *Attorney, Agent, or Firm*—Fish & Richardson P.C.

(57) ABSTRACT

Systems and methods provide audio-visual distraction to a patient while the patient is undergoing a surgical or other such medical procedure. When used in the context of a surgical procedure, local anesthetics are used to eliminate the pain of the procedure, autonomic blockade (beta blockers and/or alpha-2 agonists) is used to control autonomic responses, and audio-visual distraction is provided to distract the patient. The system allows reduction in the need for pharmacologic sedation.

8 Claims, 9 Drawing Sheets

AUDIOVISUAL DISTRACTION IN PATIENTS UNDERGOING SURGERY WITH REGIONAL ANESTHESIA

CROSS-REFERENCE TO RELATED APPLICATION

This application claims priority from U.S. Provisional Patent Application Ser. No. 60/560,882, filed Apr. 9, 2004, the contents of which are incorporated herein by reference.

GOVERNMENT RIGHTS

This work was supported by the U.S. Department of Veterans Affairs and the Federal Government has certain rights in this invention.

TECHNICAL FIELD

This invention relates to devices and techniques for providing anesthesia during surgical procedures.

BACKGROUND

Anesthesia is the process of making a patient insensible to pain and other sensations. It is the creation of a condition in which painful, traumatic, stressful, unpleasant, boring, or frightening experiences are made palatable. This process is commonly achieved with drugs both general and local. The process also requires modification of the autonomic nervous system to eliminate sympathetic and parasympathetic responses to the painful stimulus.

If a patient has been rendered insensate to the surgical stimulus through use of a local anesthetic, and the autonomic nervous system is blocked through the use of adrenergic blockade, alpha-2 agonists and vasodilators, there is still the problem of psychological distraction from the actual surgical process. Surgery can be very boring or frightening to patients. Patients are frequently given general anesthesia, simply because the case is long, and the anesthesiologist assumes the patient will not want to lie still for several hours.

People have tested and used music to provide distraction for surgical and dental procedures. Dentists use audiovisual distraction systems for dental care. There are numerous head mounted displays for use in other situations. We have not found a description of the use of audiovisual anesthesia in the operating room.

SUMMARY

The invention provides systems and methods for providing audiovisual distraction to a patient while the patient is undergoing a surgical or other such medical procedure. When used in the context of a surgical procedure, local anesthetics are used to eliminate the pain of the procedure, autonomic blockade (beta blockers and/or alpha-2 agonists) is used to control autonomic responses, and audio-visual distraction is provided to distract the patient. The system allows the reduction in the need for pharmacologic sedation.

In a first aspect, the invention provides a head-mounted display device that is adapted to provide audio and visual distraction during surgical, medical, radiologic, radiation therapy, oral surgical, and dental procedures. For use in such applications, the display device is adapted such that it may be approved for medical use.

In various implementations, the head-mounted display device may have a head strap that allows patients to lie in supine, prone, or lateral position. The device may be molded to the shape of a patient's face to prevent looking around screen. The device is preferably opaque to block outside light. The device may be designed so that it does not block operative field during neurosurgical procedures or other procedures on the head. The head-mounted display device may also include an active noise reduction system. The system would have one or several microphones that records ambient room noise. Microphones could be placed on the display unit or on a control unit. A digital signal processing system would calculate the appropriate signal to cancel ambient room noise. The cancellation signal would be added to audio sound track from audio-visual distraction to cancel room noise. The head-mounted display device may include disposable parts for replacement after use.

The device is capable of providing audiovisual distraction which is synergistic with other sedative, regional, or local anesthetic techniques reducing the dose and need for pharmacologic anesthesia. Alternatively, the device may provide audio and visual distraction during painful procedures which supplements regional or local anesthetic techniques reducing the need for or dose of pharmacologic sedation. The device may also reduce patient movement during radiology, radiation therapy, MRI, or other medical procedures, which may or may not be painful or uncomfortable but where patient movement will be a problem. The device may reduce fear and anxiety and claustrophobia during medical procedures.

In a second general aspect, the invention provides a head-mounted image display device comprising a head-mountable assembly that when worn by a patient occludes the patient's view of surroundings, and an image generator on the assembly for producing an image viewable by the patient, wherein a center of gravity of the head-mounted image display device is positioned to enable use by the patient in a supine, lateral, or prone position.

In a third general aspect, the invention provides a system that provides controlled and appropriate media for medical procedures from networked source. Such a system has the ability to play various type of recorded media, such as VHS tapes, DVD, CD disks, digitally compressed, or other formatted material. The system comprises a head-mounted image display device that when worn by a patient occludes the patient's view of surroundings, the head-mounted image display device including an image generator for producing an image viewable by the patient, wherein a center of gravity of the head-mounted image display device is positioned to enable use by the patient in a supine, lateral, or prone position. The system further comprises a media source device capable of being connected to the head-mounted image display device to provide media for the image generator to produce the image.

The system may record the use of specific media, the specifics of the use, and provides information to allow payment of royalty fee, and analysis of usage patterns. The system may also have security features to prevent dissemination, distribution, or copying of copyrighted material. The media may be general use or custom media appropriate and specific for selected use.

In addition to providing patient video distraction, the system may also monitor and record ECG and blood pressure from the networked connection to anesthesia monitors to provide alarms and warning if the patient's heart rate and blood pressure are elevated during the procedure. Another embodiment of the device has the ability to measure ECG and blood pressure to provide warning of elevated heart rate and blood pressure during procedure.

In addition, the system may monitor EEG and or ocular myographs (muscle recordings) and or monitor eye lid position. If patient was falling asleep audio and video signal can be diminished or tapered to allow natural sleep. Active noise reduction from digital signal processor would suppress ambient room noise. Change would be gradual with feedback to allow for natural sleep.

The system may have timing of audiovisual programs that allow for different case lengths. Also, the system may shift immediately from one media selection number to another to prevent the patient from loosing the distraction effect. Longer selections or selections with a series of sequels may be used for cases with expected longer durations.

The details of one or more embodiments of the invention are set forth in the accompanying drawings and the description below. Other features, objects, and advantages of the invention will be apparent from the description and drawings, and from the claims.

DETAILED DESCRIPTION

Figure 4A:
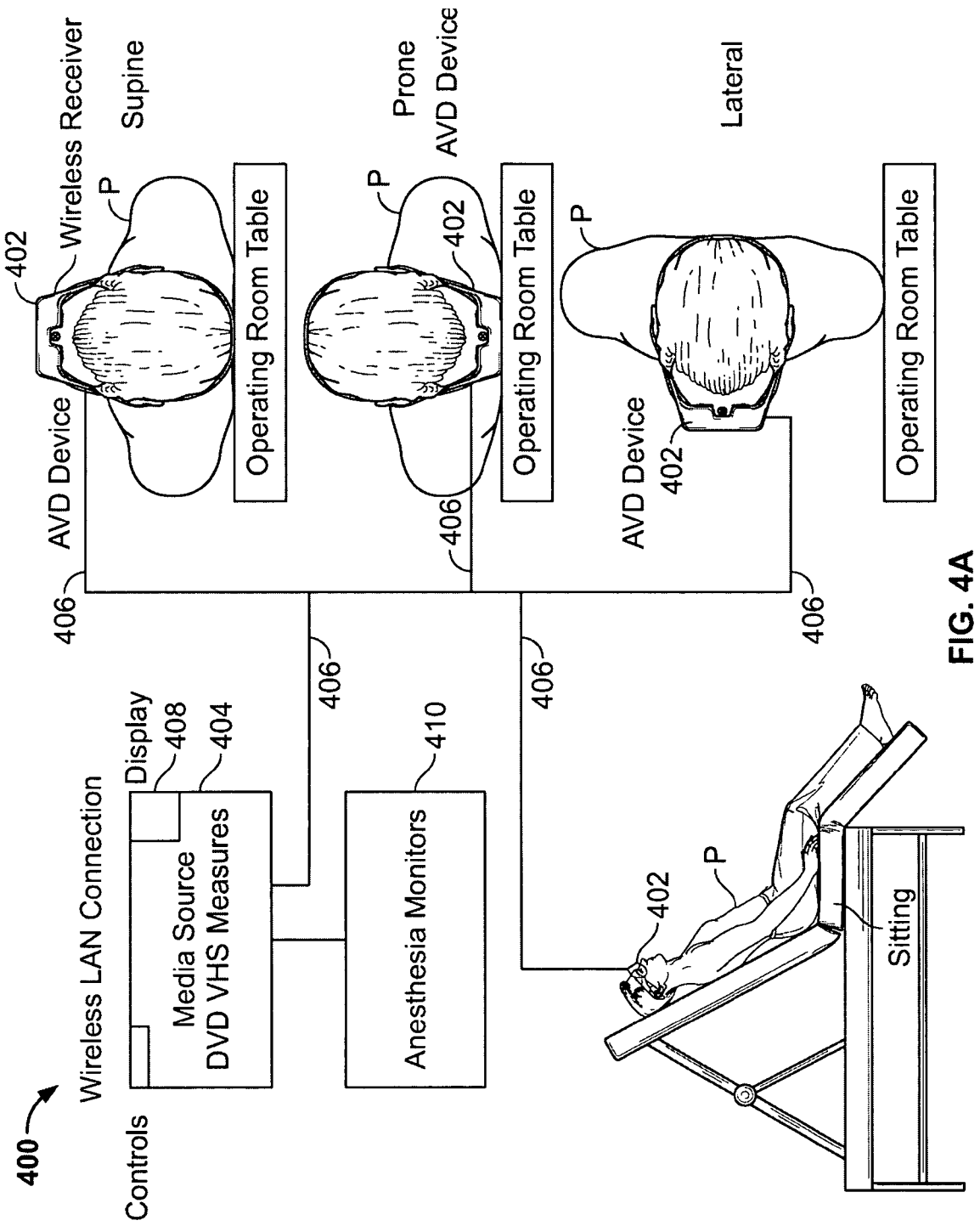
FIG. 4A is a block diagram of a system in accordance with an aspect of the invention for providing audio-visual distraction to multiple patients wearing head-mounted display devices.

As shown in FIG. 4A, an exemplary system 400 includes one or more sets of glasses 402 having a TV screen and ear phones for sound. Here, each set of glasses 402 is worn by a patient P. There is a media source device 404 to play movies, of the patient's choice. The glasses sets 402 are connected to the media source device 402 through a connection 406. The system can be used for surgical, medical, cardiologic, gynecologic, radiological, nuclear medicine, radiation therapy, dental, or other procedures. The media source device 404 has a display 408 to allow an anesthetist to monitor the movie to make sure it is functioning. Also, messages may be displayed on the display 408 when the media source device 404 is connected to a patient-monitoring device 410, such as an anesthesia machine that tracks measurements of the patient's condition. The movies can be DVD, Video tapes, stored on media internal to the device, or distributed from a central repository. A large selection of movies are available to allow patients to choose what they want to see.

Figure 4B:
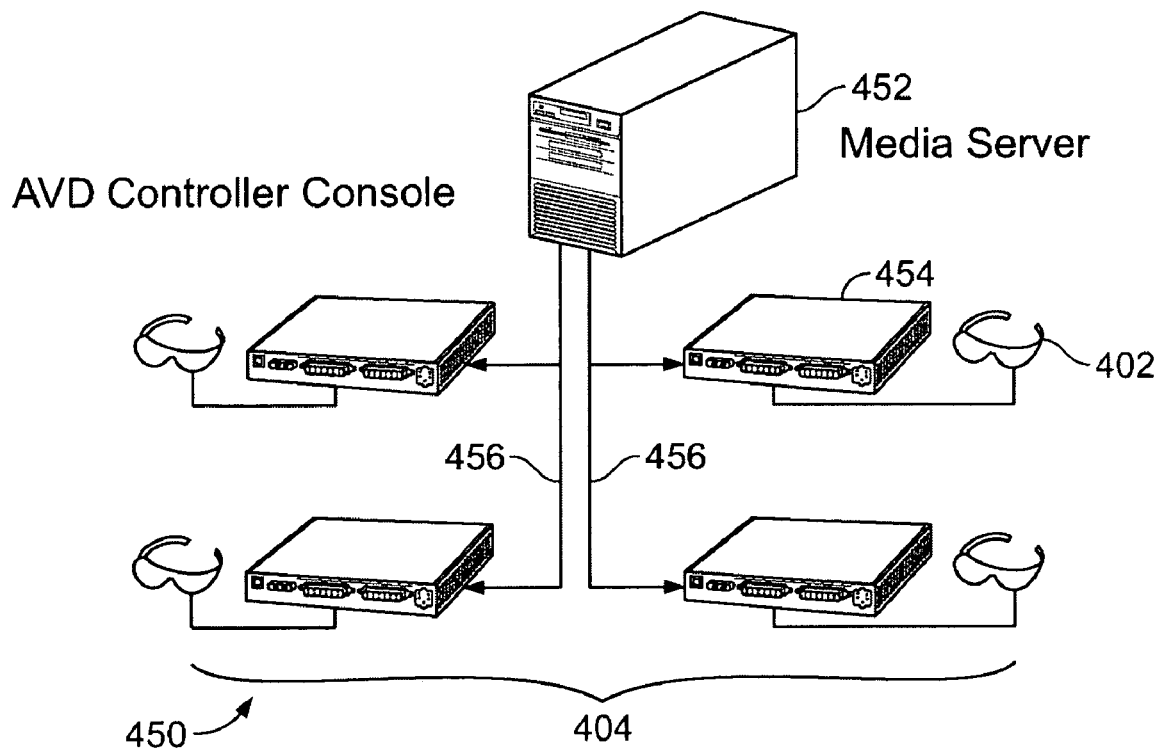
FIG. 4B is a block diagram of another system in accordance with an aspect of the invention.

Another system 450 is shown in FIG. 4B. Here, the media source device 404 includes a server device 452, and one or more console devices 454 connected to the server device through one or more connections 456, for example a computer network. Any or all of the console devices 454 can have a set of glasses 402 connected to them. In use, the server device provides the console device(s) with the media for the image generator (such as a TV screen) in the glasses to produce the image viewable to the patient.

Figure 1:
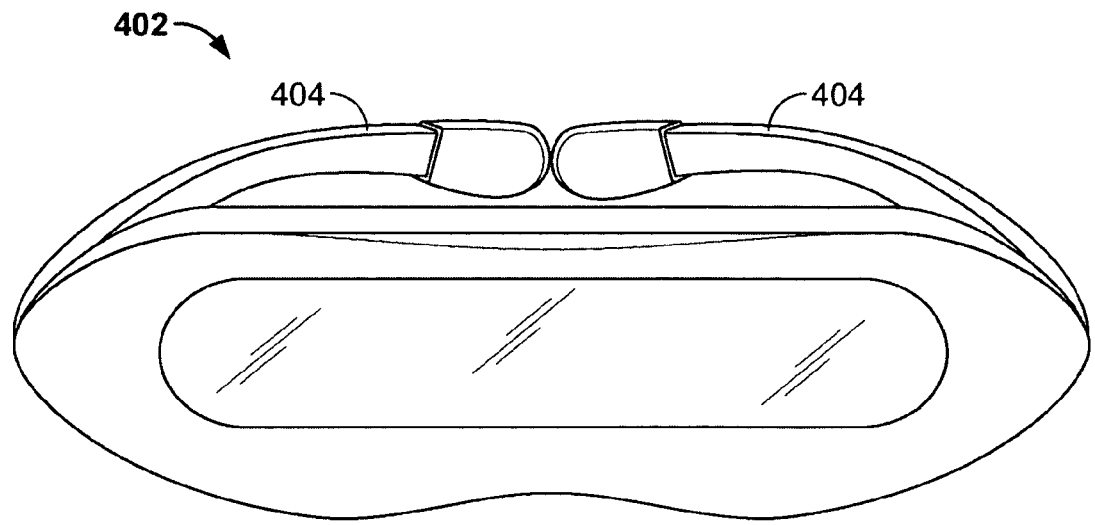
FIG. 1 shows an embodiment of a head-mounted display device in accordance with an aspect of the invention.
Figure 2:
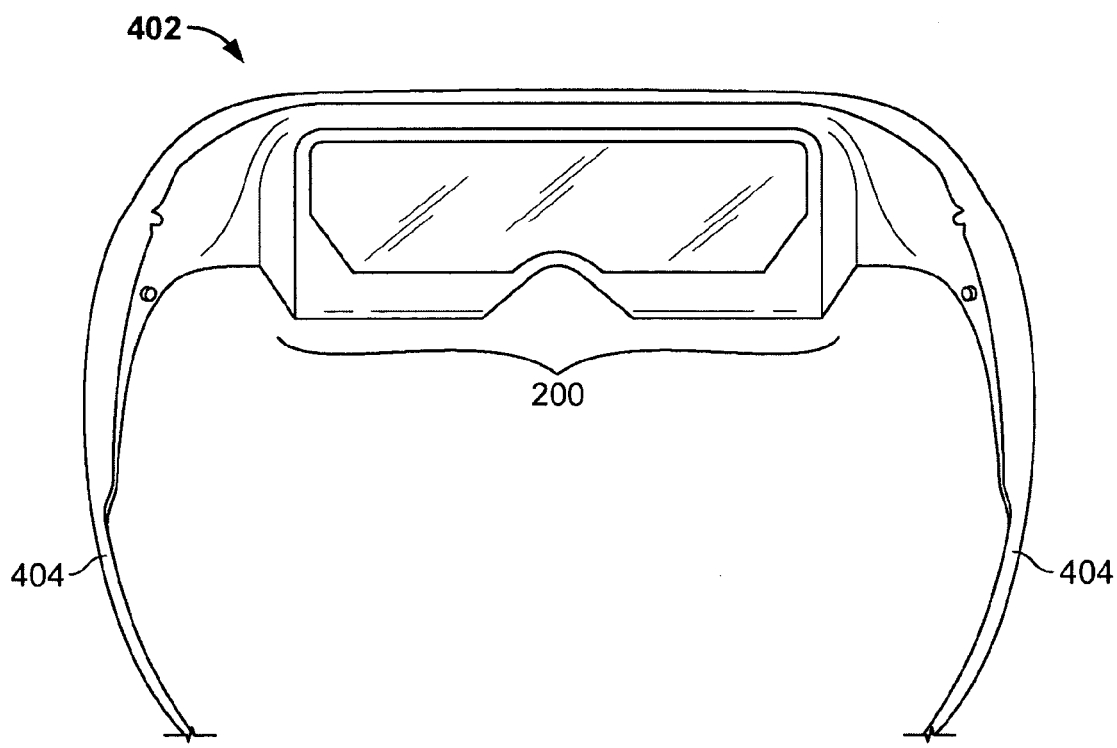
FIG. 2 shows the device of FIG. 1 from a different view.

An exemplary set of glasses 402 is shown in FIGS. 1 and 2. When worn by a patient, the glasses 402 occlude the patient's view of the surroundings. Moreover, the glasses has an image generator 200 for producing an image viewable by the patient. For example, the image generator may be a TV screen that is small enough to be fitted inside the glasses. FIG. 1 is a frontal view of the glasses 402 where braces 404 can be seen extending toward the rear. FIG. 2 is a view from above.

In some implementations, the set of glasses 402 except the image generator 200 is configured to be disposable after use. One advantage of this is that it eliminates the need to clean the glasses for use by the next patient. After use, the image generator 200 may be removed from the glasses 402. The remainder of the glasses 402 may thereafter be discarded and the image generator may be inserted in another set of glasses 402 for the next use. For example, any portion of the glasses 402 that touches the patient during use may be made disposable.

The system has electrical isolation for use in the operating room. It has electrical shielding to eliminate interference from electrical surgical cautery. The shielding is provided around the connection 406, such as a cable, from the media source device to the glasses and over the ear phone connections. This shielding can be either a passive or active driven ground. Electronics in the head mounted display can be shielded as well either by doping the plastic with metals to make them conduct or by encasing the electronics in conductive materials. The system can be optically isolated to protect the patient from microshocks. The network connection can also be electrically isolated using either optical or other techniques to prevent the possibility of ground loops. It has a volume control for the head phones for the patient.

The balance (center of gravity) of the glasses may be established to allow wearing in the supine, prone, lateral, or sitting position. A pillow with a cut out for the ear and ear piece with a support is provided to allow lateral position. The glasses are opaque so as to block look-around vision from the top, sides, and inferior aspects. The retaining strap can be moved to allow access to the skull for craniotomies, the ear for auditory procedures. A single screen version (left or right) could be used for ocular procedures.

Figure 5:
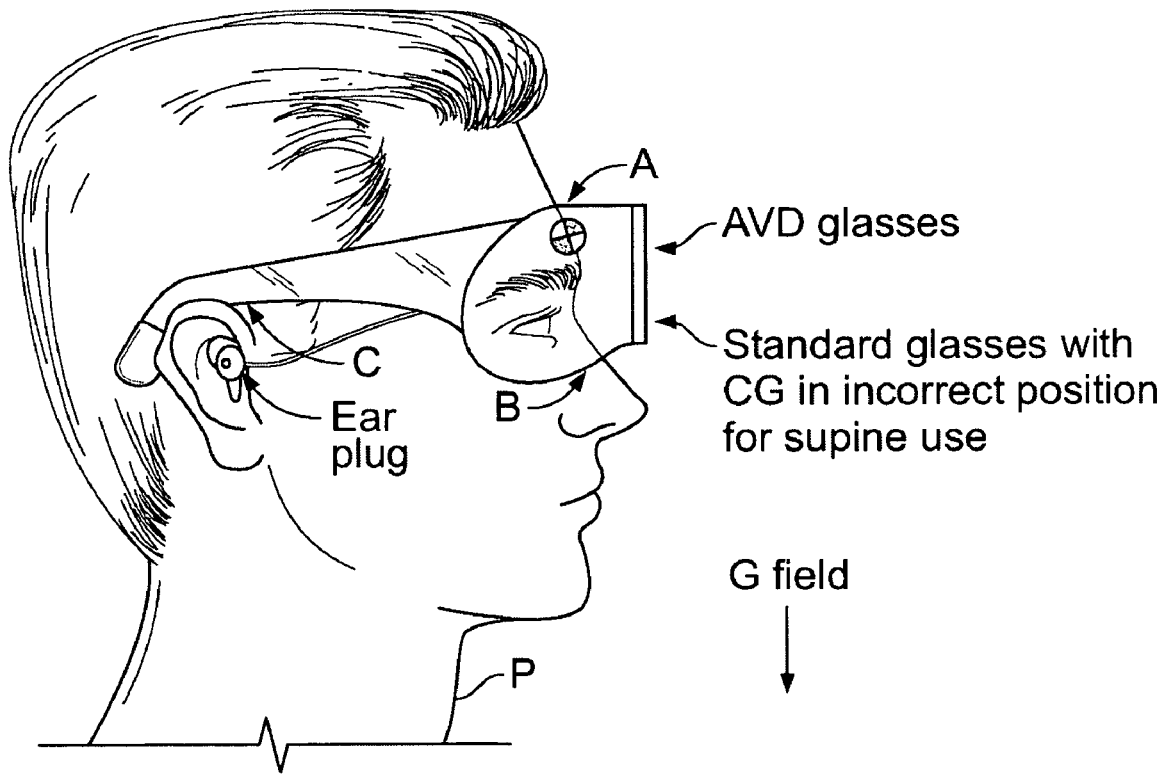
FIG. 5 is a diagram of the problems with current audiovisual eyeglass systems. The center of gravity is anterior to the patient's face providing a moment of rotation when used in the supine position.
Figure 6:
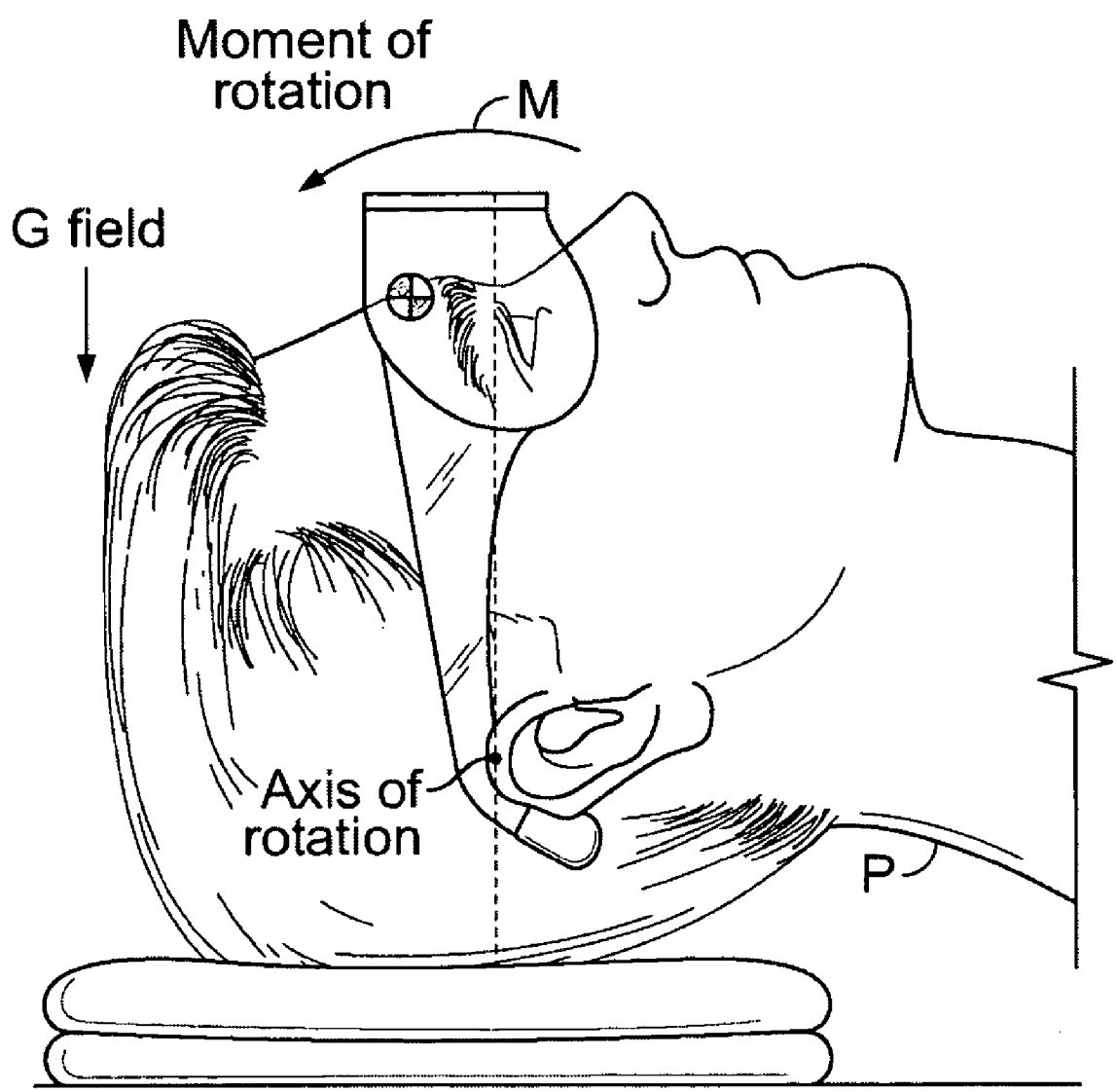
FIG. 6 is a diagram of the problems with current audiovisual eyeglass systems when used in the supine position. The glasses rotate towards the top of the head.

Referring to FIG. 5, a patient P is shown with a prior art head-mounted display device being worn by a person in an upright position. As seen, the center of gravity, as indicated in the figure by a circle cut in quarters with two of the quarters shown black, must be behind the bridge of the person's nose (A). The load is therefore carried on the bridge of the face, the bridge of the nose (B), and ears (C). This center of gravity positioning will not work well for supine use. As shown in FIG. 6, using a standard head-mounted display device with the center of gravity as indicated when a patient P is in the supine position causes rotation superiorly, as indicated by an arrow M in FIG. 6, because the center of gravity is superior to the axis of rotation.

Figure 7:
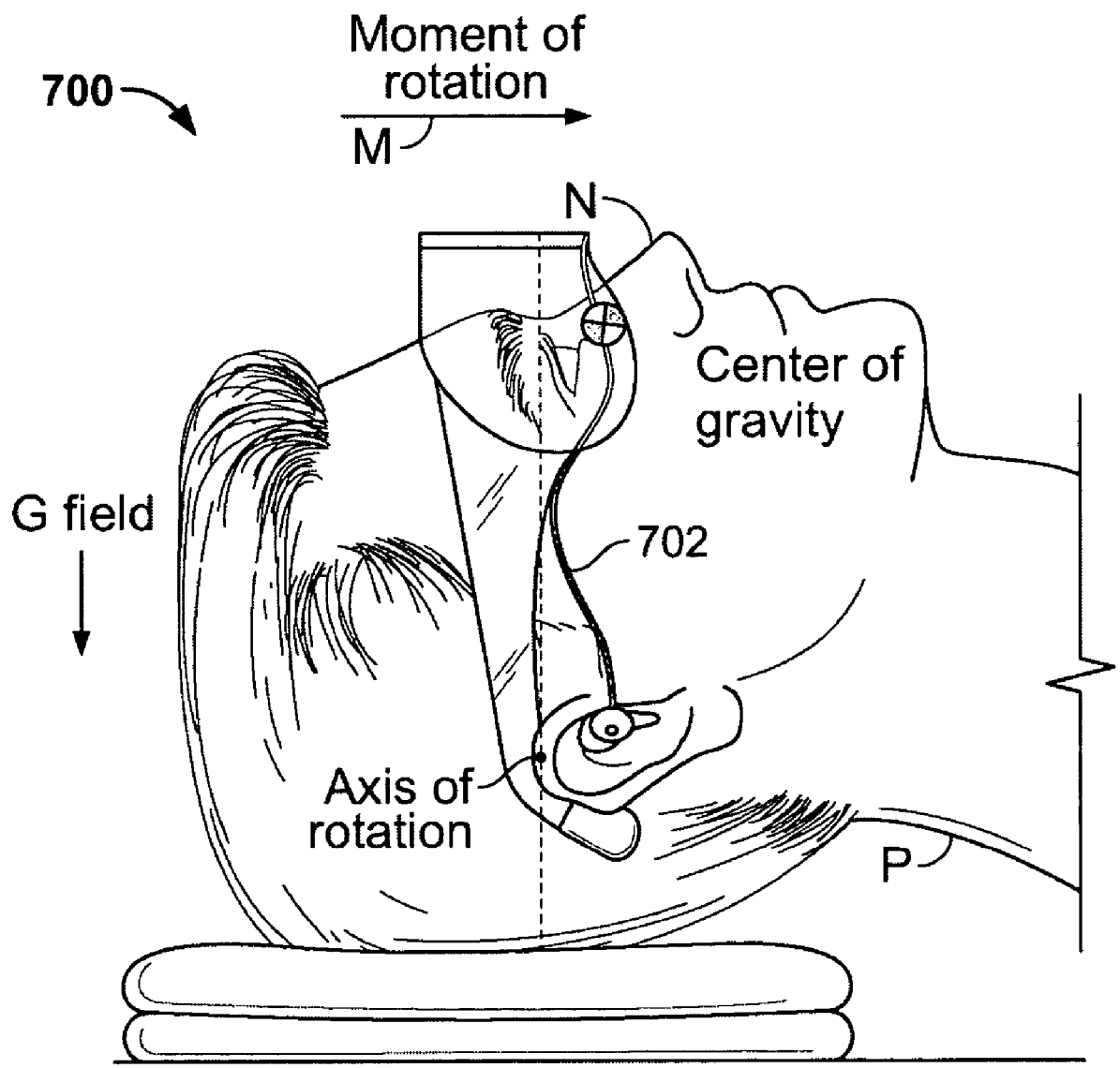
FIG. 7 is a diagram of an embodiment of an inventive system with the center of gravity close to the face and inferior to the axis of rotation around the ears. Movement of the center of gravity towards the face and inferior eliminates rotations when glasses are used in the supine position.

FIG. 7 shows a patient P in a supine position wearing a head-mounted display device 700 that is an embodiment of an aspect of the invention. In this example of the display device, the center of gravity is positioned between the patient's eye and nose. Moreover, a moment of rotation M is more towards the bridge of the nose. This prevents the head-mounted display device from riding up onto the patient's forehead when the patient is in the supine position. Also, the device 700 includes earphones 702 connected to the glasses.

Figure 8:
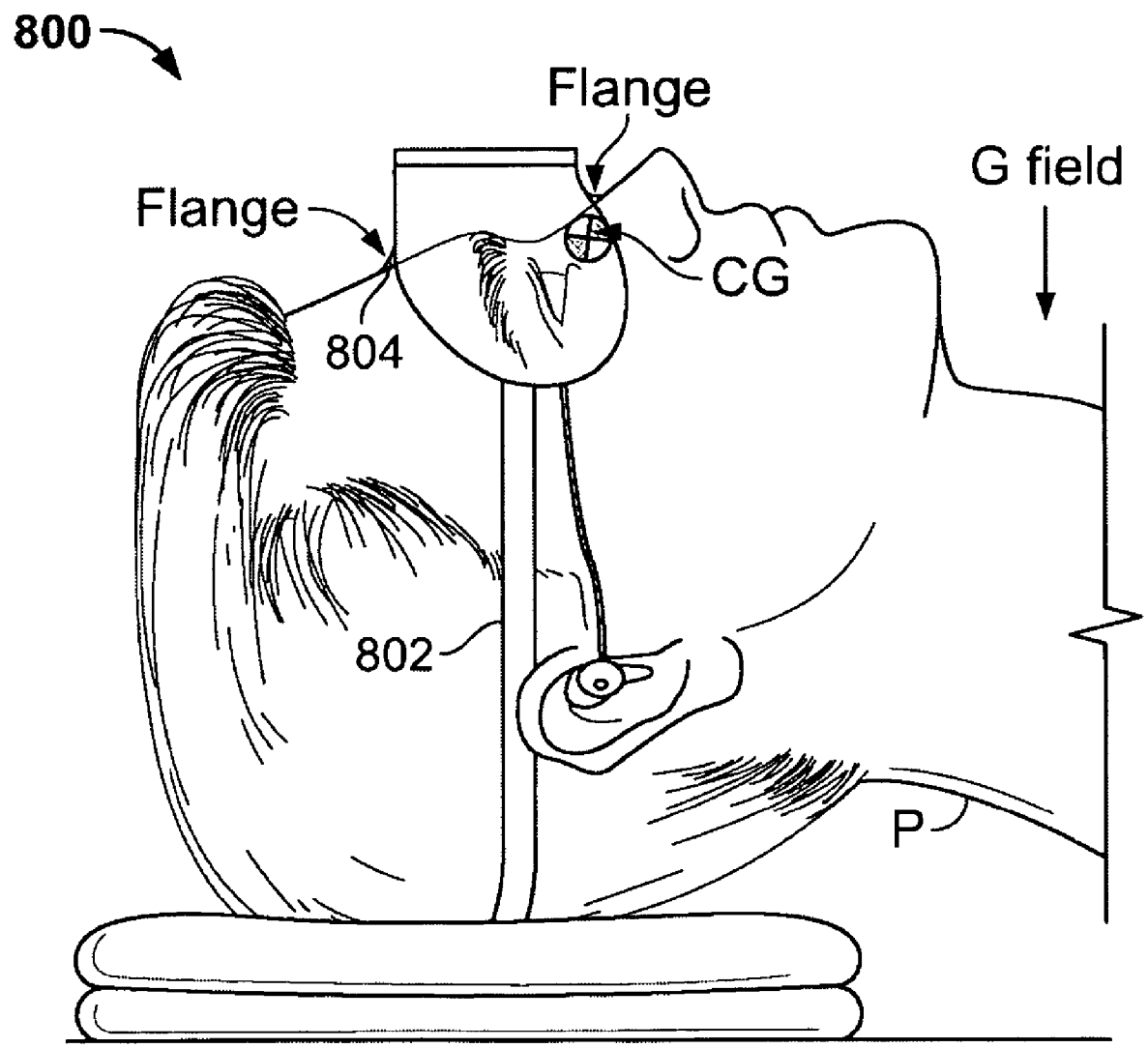
FIG. 8 is a diagram of an embodiment of an inventive system with a flange for increased comfort and to provide a surface to allow the use of tape to adhere the glasses to the face. The system also shows a simple band head strap which allows access to the head for cranial procedures or ears for otolaryngotic procedures.

FIG. 8 shows a head-mounted display device 800 that is an embodiment of an aspect of the invention. Here, a head strap 802 allows the patient P to retain the glasses while in supine, lateral, and prone positions. It also allows movement of the strap for operations where it will be in the operative field (or near it). One or more flanges 804 on the glasses will allow load distribution to make them more comfortable to wear. Flanges also allow for retention to the patient's face using tape. Use of tape to hold the device to the face will eliminate the strap from the operative field.

Figure 9:
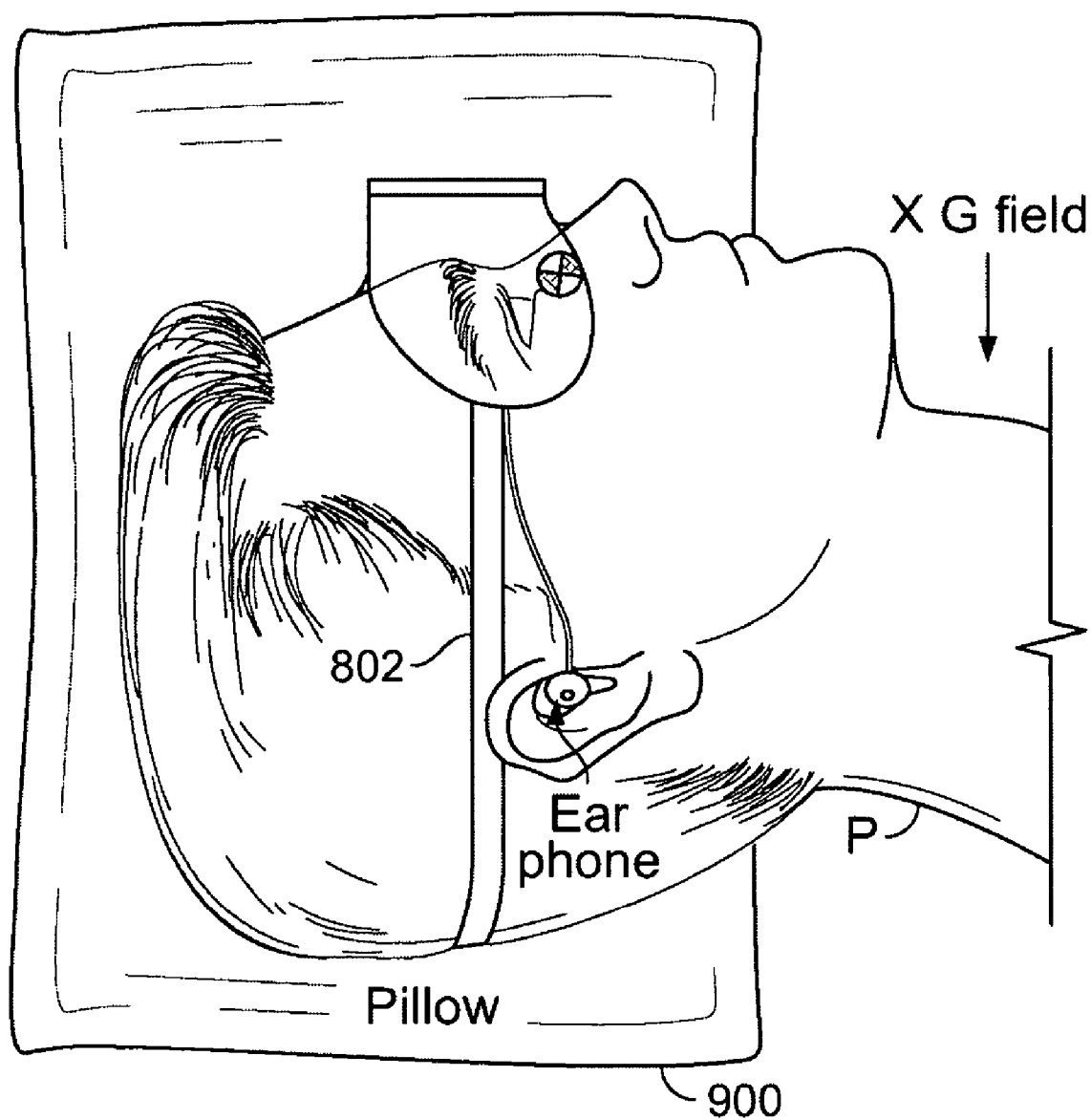
FIG. 9 is a diagram of the use of the FIG. 8 system in the lateral position. View is from the side. The center of gravity is close to the face and near the bridge of the nose to reduce rotations. There is a cut out in the pillow to allow use of the audio ear phone in the lateral position.

FIG. 9 shows the patient P in the lateral position on a pillow 900. The strap 802 improves patient comfort. The strap will eliminate or reduce the torque that may otherwise develop between the pillow and the frame of the head mounted display device.

Figure 10:
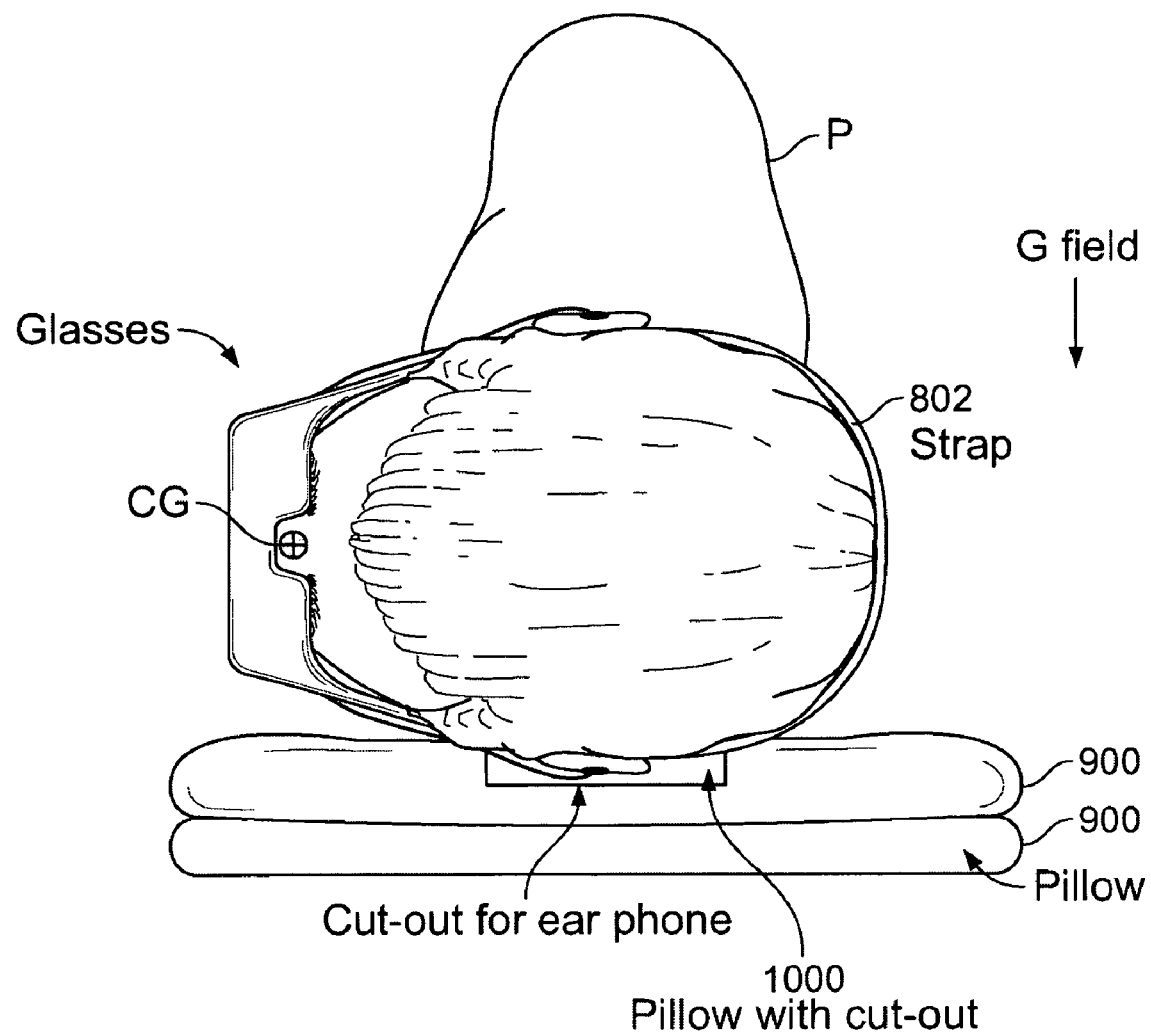
FIG. 10 is a diagram of the use of the FIG. 8 system in the lateral position. View is from the top of the head. The cut out in the pillow for use of the audio ear phone is detailed.

FIG. 10 shows a view of the top of a patient's (P) head lying on two pillows 900. The pillow may have a shape that accommodates the head-mounted image display device. For example, the pillow 900 that is nearest the patient's head may have a cut-out 1000 in it to improve the comfort of the ear phone in the dependent ear. As shown, the cut-out 1000 allows the patient's ear to be comfortable with an ear phone in place. The center of gravity, in this example, may be close to the face to reduce torques away from the patient's face.

The system may also be used in the post operative recovery room. Use in the post operative recovery room reduces the irritation and boredom patients feel while waiting for spinal or epidural anesthesia to resolve. The patient's identifying information would cue the video server to restart the media at the same location as where the patient left off in the OR. If the patient wants to watch prior to the procedure, the movie can be continued in the OR, and then in recovery by entering the patient's identifying information to restart the media in the exact position in the media of choice.

Figure 3:
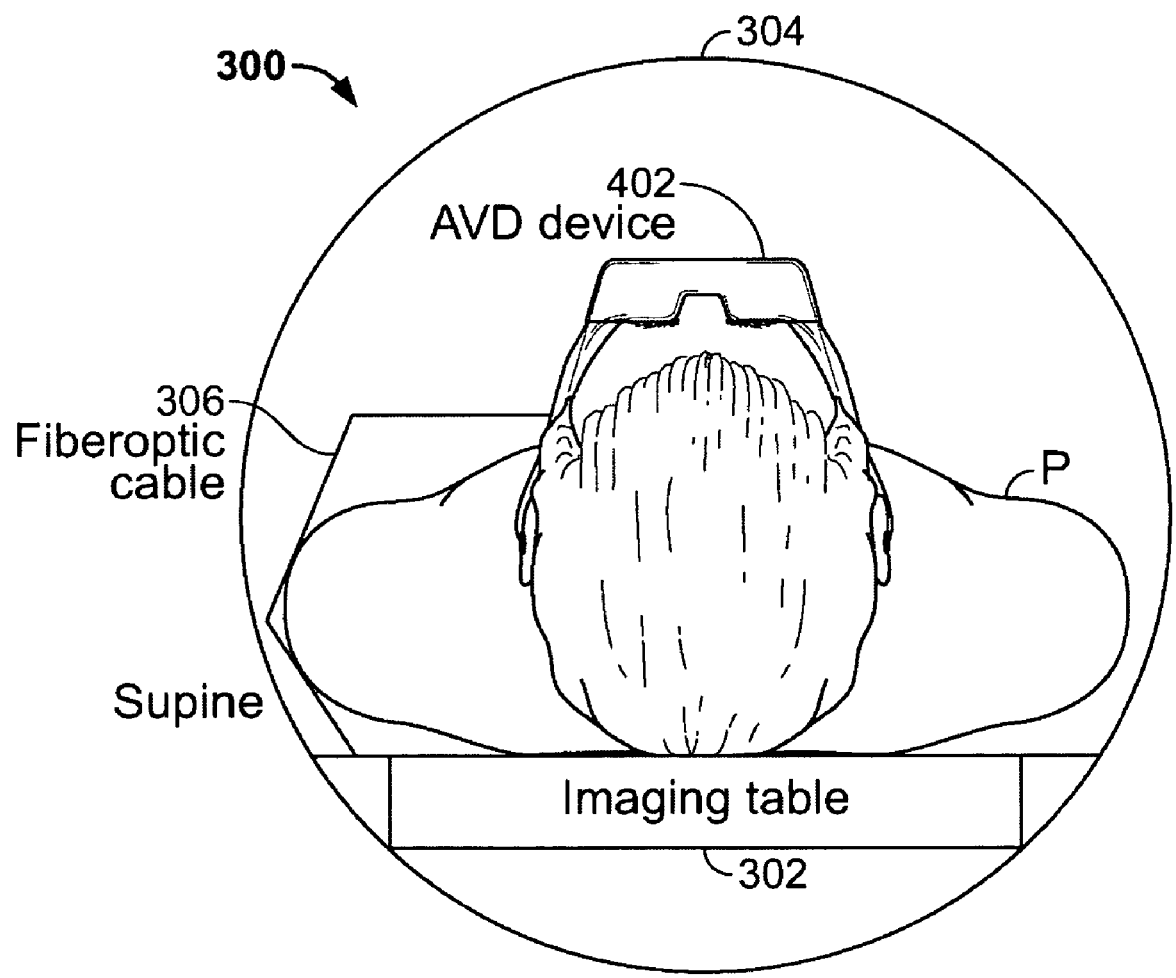
FIG. 3 is a diagram of a patient within an imaging system and wearing a device in accordance with an aspect of the invention.

FIG. 3 shows an embodiment system 300 of an inventive aspect that is MRI compatible. The patient P is currently using the system 300 while in a supine position on an imaging table 302 inside an MRI chamber 304. This system may use one or more optical fiber cables 306 to provide the audiovisual feed. For example, a fiber-optic light pipe with coherent fibers may provide the video feed from the media source device to the image generator in the set(s) of glasses. Acoustic signal may also be available. The head set may use passive optics and sound to avoid electronic signals in the MRI machine. Placing patients in MRI scanners frequently invokes claustrophobia, but the audiovisual anesthesia system provides distraction which will reduce anxiety and reduce the need for pharmacologic sedation. Such a system may therefore allow the patient to undergo magnetic resonance imaging with less need for sedation.

The system is easy to use. The anesthetist, nurse, doctor or dentist simply hooks up the standard monitors, places the video goggles on the patient, and then cues up the movie of choice. The same movie of choice can be cued up on the post operative recovery room.

The following is an example of how procedure works:
1) Patient is taken into operating room,
2) Video feed started,
3) Monitors placed,
4) Regional or local technique administered.
5) Patient monitored for effect and need for additional medications.

The head-mounted display device incorporating various of the above-described features affords advantages not afforded by prior art head-mounted display devices. Some of the disadvantages of prior art devices that are overcome by one or more of the features of the invention described above include the following:

a. The center of balance is designed for upright posture.— Most OR cases are done in the supine, prone, or lateral position. In each of these positions the glasses slide off the patient or are painful to lie upon (lateral position).

b. There is a bracket on top of the head or near the temple.— This bracket is painful to lie on and interferes with surgical procedures on the skull, brain, ears, eyes or other cranial structures.

c. The eye glass systems allow peer around. Patients do not want to see around the glasses, they want to be distracted by the system and don't want to see their surroundings.

d. There is no electrical noise protection. The operating room is a high electrical noise environment and the electro-cautery may interfere with the video signal.

The set of glasses 402 may be made with an opaque black plastic frame much like a pair of safety goggles. This shape will fit to the face and provide block out of peripheral vision. It will rest comfortably on the face in supine position. It will provide a strap to hold the device on the face in prone position. Comfort will be improved in lateral decubitus position because the strap will be flat and not put pressure on the side of the head. The flange on the face provides a surface that can be taped to the face to avoid motion of the device.

A pad with a cut out for the ear and ear piece will improve comfort in the lateral position.

Alternatives:
1. The media could differ. The media could include music alone, music videos, media designed specifically to hypnotize patient, sports, adventure, entertainment, etc. The media content is important. It should be engrossing and uninterrupted. Different population groups want different media content. Men prefer content with action, adventure, and violence. Women prefer content with music, beauty, love, romance, and emotion. Children prefer cartoons. Older patients prefer different content than younger patients. The most important feature of the media is that it is engrossing to the subject.
2. The media could be by subscription. The media could be downloaded from a server. The media could be from tapes, DVD's, CD's, internet, satellite, subscription, etc. The system may record information about the use of the media, the patient's response, or both, and use this information for some purpose. The information can be used for billing, quality assurance, safety monitoring, and optimization of the system and the media, to name just a few examples. The recorded information can be downloaded from the system as necessary.

3. The media may be tailored to the use to optimize the distraction technique.
4. Delivery of the content may be from a video server. The operator would have a list of titles with brief characterizations (comedy, action adventure, chick flick, cowboy, musical, romantic comedy, etc). The operator then chooses a selection from the list which is served up by the media server. There is a screen to monitor the content to ensure it is working and appropriate. The screen also allows operation instructions to the operator.
5. The content may be provided by the operator or patient and placed in the system.
6. The system could be MRI compatible using fiber optic (non ferromagnetic) cabling. The head set would then consist of lenses and prisms to provide an image. The video production device would have a light source, lens system, transparent liquid crystal chip to generate the image. The image would be transmitted to the head set by coherent fiber-optic cable. The acoustic signal would be through conductive air tubes or another technique.
7. The head set may be useful for other purposes as well. For example, laser or welding eye injury is a serious problem. The video head set could have a video camera connected to drive the eye glass system. The operator would see only images transmitted through the video system. The eyes could be completely covered. Such a system could be used to avoid laser injury, welding injury, flash injury in military laser use, etc. Providing a completely synthesized visual signal can prevent photo or mechanical injury to the eye and specifically cornea and retina.
8. Three dimensional photography could be viewed on the eye glass system. With the advent of electronic cameras, dual lens cameras could store dual images electronically and be replayed on the eye glass system.
9. Other sensory stimulation may assist in distraction. Olfactory stimulation could be by means of chemicals, electrically generated smells, vapors provided by tube delivery to the device. Electrical or mechanical stimulation of the skin can be distracting as well.
10. Autonomic monitoring and blockade is important in all anesthetic care. The system could download data from the anesthesia monitoring system or have an independent monitor of heart rate, blood pressure, respiratory rate. Warnings could be generated by absolute cut offs such as heart rate greater than 100 beats per minute, or by changes in monitored parameters such as heart rate has increased by 20%, respiratory rate less than 8 breaths per minute, systolic blood pressure too high or low, ECG ST segments elevated or depressed by 0.1 mvolt. The operator could be warned of the problem, for example through a message presented on the display 408.
11. The system can include active noise suppression with microphones either on the eye gasses or on the control unit to record ambient noise. Active digital filtering will suppress the room noise by providing the interfering noise signal.
12. Eye motion, ocular myograms, or electroencephalograms will be recorded to detect the onset of natural sleep. If the patient falls asleep the sound and video levels can be tapered to allow natural sleep. If the patient awakens the video and audio signal would be continued from the point of onset of sleep. For example, the patient-monitoring device 410 can monitor whether the patient falls asleep during the operative procedure. When the patient falls asleep, the patient-monitoring device 410 can alert the media source device 404 to interrupt the transmission of media, for example by stopping the presented movie. The media source device 404 can track the point in the media where the patient fell asleep; when the patient again wakes up, the media source device can restart from where it was interrupted.

Fundamental Content:

1. Audiovisual system to deliver sound and images to patients undergoing surgical, medical, dental, gynecologic, endoscopic, radiologic, nuclear medicine, radiation therapy procedures or other procedures. The system distracts, amuses, hypnotizes, stimulates, or sedates patients undergoing boring, painful, stressful, uncomfortable, frightening, claustrophobic, or emotionally difficult procedures. It is a form of electronic anesthesia.
2. System to deliver content to audiovisual system. Content is tailored to patient interest, needs, and situation.
3. System allows the reduction in sedation. Pain is controlled through local anesthetics or systemic agents. Autonomic blockade is provided by beta blockers, alpha-2 agonists, ganglionic blockers, etc. Additional sedatives can be used to augment audiovisual distraction.

Clinical Trial:

A prospective, randomized, blinded analysis, clinical trial with two groups: audiovisual distraction (AVD) and control, was designed and conducted to study 100 patients undergoing surgery using regional or local anesthesia. The trial demonstrated that the audiovisual distraction (AVD) system provided an experience very similar to pharmacologic sedation but reduced the need for and dose of pharmacologic sedatives.

A number of embodiments of the invention have been described. Nevertheless, it will be understood that various modifications may be made without departing from the spirit and scope of the invention. Accordingly, other embodiments are within the scope of the following claims.

What is claimed is:

1. A system for use during an operative procedure, the system comprising:
a head-mounted image display device that when worn by a patient occludes the patient's view of surroundings, the head-mounted image display device including an image generator for producing an image viewable by the patient, wherein a center of gravity of the head-mounted image display device is positioned to enable use by the patient in a supine, lateral, or prone position; and
a media source device capable of being connected to the head-mounted image display device to provide media for the image generator to produce the image;
wherein the media source device is further configured to be connected to a patient-monitoring device that is used during the operative procedure.

2. The system of claim 1, wherein the media source device further includes a display presenting the image to a person participating in the operative procedure, the media source device being configured to present on the display a message triggered by the patient-monitoring device.

3. The system of claim 1, wherein the media source device is configured to be automatically interrupted upon the patient-monitoring device detecting that the patient falls asleep during the operative procedure.

4. The system of claim 3, wherein the media source device is further configured to restart upon the patient-monitoring device detecting that the patient awakens from being asleep, the media source device to restart from where it was interrupted by the patient-monitoring device.

5. The system of claim 1, wherein the head-mounted image display device is MRI compatible.

6. The system of claim 1, wherein the media source device comprises:
   a console device to be connected to the head-mounted image display device; and
   a server device capable of being connected to several console devices, wherein the server provides the console device with the media for the image generator to produce the image.

7. A system for use during an operative procedure, the system comprising:
   a head-mounted image display device that when worn by a patient occludes the patient's view of surroundings, the head-mounted image display device including an image generator for producing an image viewable by the patient, wherein a center of gravity of the head-mounted image display device is positioned to enable use by the patient in a supine, lateral, or prone position;
   a media source device capable of being connected to the head-mounted image display device to provide media for the image generator to produce the image; and
   a pillow for the patient to use during the operative procedure, the pillow having a shape that accommodates the head-mounted image display device.

8. A system for use during an operative procedure, the system comprising:
   a head-mounted image display device that when worn by a patient occludes the patient's view of surroundings, the head-mounted image display device including an image generator for producing an image viewable by the patient, wherein a center of gravity of the head-mounted image display device is positioned to enable use by the patient in a supine, lateral, or prone position; and
   a media source device capable of being connected to the head-mounted image display device to provide media for the image generator to produce the image;
   wherein the media source device records information regarding at least one of i) use of media and ii) patient response and uses this information for at least one selected from the group consisting of: billing, quality assurance, safety monitoring, and optimization of the system and the media.

* * * * *